United States Patent [19]

Alvarez et al.

[11] 4,096,166

[45] Jun. 20, 1978

[54] PROCESS FOR THE PREPARATION OF CARBAMATES OF N-HYDROXYTHIOIMIDATES

[75] Inventors: Jose Rafael Alvarez, Charleston, W. Va.; Julius Jakob Fuchs, Wilmington, Del.

[73] Assignee: E. I. Du Pont de Nemours and Company, Wilmington, Del.

[21] Appl. No.: 728,948

[22] Filed: Oct. 4, 1976

Related U.S. Application Data

[63] Continuation-in-part of Ser. No. 546,997, Feb. 4, 1975, abandoned.

[51] Int. Cl.$^2$ .................. C07C 69/00; C07C 121/38
[52] U.S. Cl. .................. 260/453 RW; 260/465.4
[58] Field of Search .................. 260/453 RW, 465.4

[56] References Cited

U.S. PATENT DOCUMENTS

| | | | |
|---|---|---|---|
| 3,506,698 | 4/1970 | Jelinek | 260/453 RW |
| 3,530,220 | 9/1970 | Buchanan | 260/465.4 |
| 3,557,190 | 1/1971 | Buchanan | 260/453 RW |
| 3,576,834 | 4/1971 | Buchanan | 260/453 |
| 3,658,869 | 4/1972 | Soloway et al. | 260/453 |
| 3,752,841 | 8/1973 | Fuchs | 260/465.4 X |
| 3,787,470 | 1/1974 | Buchanan | 260/453 |
| 3,852,317 | 12/1974 | Zanker | 260/453 P |
| 3,890,362 | 6/1975 | Alvarez | 260/453 RW |

FOREIGN PATENT DOCUMENTS

| | | | |
|---|---|---|---|
| 1,912,294 | 10/1969 | Germany | 260/465.4 |
| 1,090,986 | 11/1967 | United Kingdom. | |
| 1,208,862 | 10/1970 | United Kingdom. | |

OTHER PUBLICATIONS

JACS, 72, 1888–1891 (1950).

*Primary Examiner*—Elbert L. Roberts
*Assistant Examiner*—Robert C. Whittenbaugh

[57] ABSTRACT

An improved process for converting N-hydroxythioimidates to N-(methylcarbamoyloxy)-thioimidates by reaction with methylcarbamoyl chloride at pH above 10 in a two-phase reaction medium: water and a water-immiscible organic solvent.

5 Claims, No Drawings

PROCESS FOR THE PREPARATION OF CARBAMATES OF N-HYDROXYTHIOIMIDATES

CROSS-REFERENCE TO RELATED APPLICATIONS

This application is a continuation-in-part of applicant's copending application Ser. No. 546,997 filed Feb. 4, 1975, now abandoned.

BACKGROUND

The preparation of carbamates of N-hydroxythioimidates by three generally applicable methods is known in the art: U.S. Pat. No. 3,576,834 and British Pat. No. 1,090,986:

(1) Reaction of the N-hydroxythioimidate with an isocyanate and a basic catalyst in an inert, anhydrous organic solvent, at elevated temperatures.

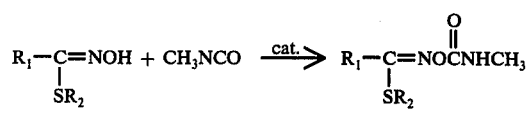

(2) Preparation of the N-hydroxythioimidate salt in aqueous solution, reaction of this aqueous solution with phosgene in a water immiscible organic solvent at 0°–5° C, separation of the organic layer containing the chloroformate ester, and reaction of this organic layer with an aqueous solution of an amine at 0°–5° C.

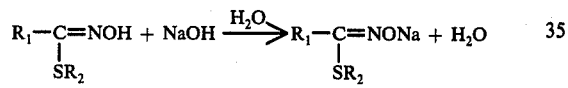

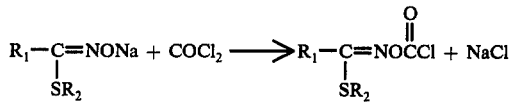

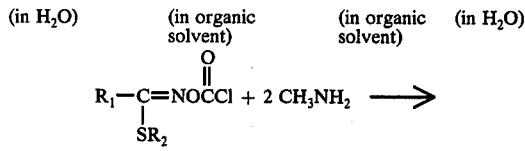

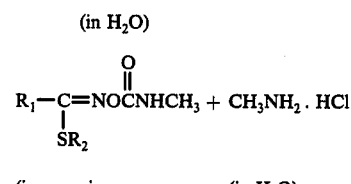

(3) Preparation of the salt of the N-hydroxythioimidate in an inert anhydrous organic solvent using sodium hydride or sodium amide as base; reacting this salt with a carbamoyl chloride.

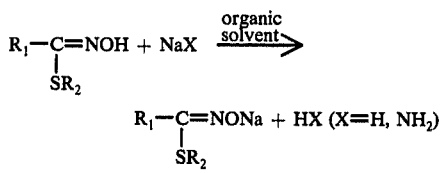

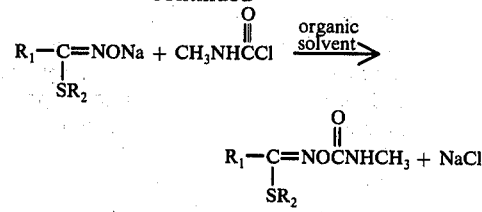

Methods (1) and (3) require expensive reagents ($CH_3NCO$, NaH) and anhydrous conditions. Although a partially aqueous reaction medium is permitted in method (2), the reaction must be conducted at low temperature and involves the handling of poisonous phosgene.

Also, if a chemist skilled in the art adapted the reaction of an N-hydroxythioimidate with a carbamoyl chloride to an aqueous or partially aqueous system, he would expect the following side reactions to take place:

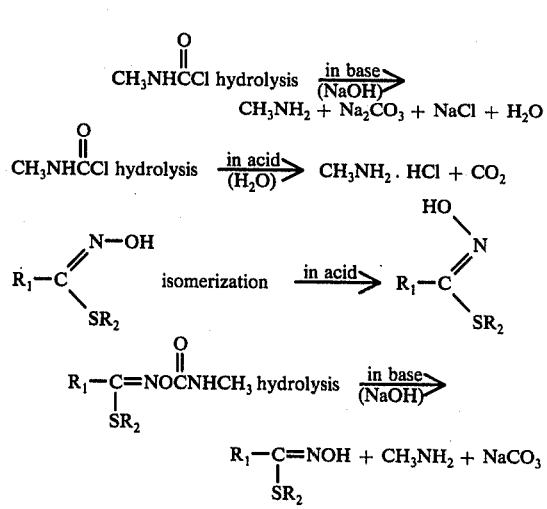

Further, it is known in the art that carbamoyl chlorides are destroyed by bases, particularly aqueous alkali. British Pat. No. 1,208,862 teaches that carbamoyl chlorides dissolved in a water-immiscible organic solvent and contacted with an aqueous base are transformed into isocyanates; U.S. Pat. No. 3,852,317 discusses the British Patent and discloses that isocyanates are extremely unstable in the presence of aqueous alkali, and that they are converted to a great extent into carbamates and carbamic acid. Therefore, it would be expected that basic pH would destroy methyl carbamoyl chloride (or methyl isocyanate) under the reaction conditions of this application and thus reduce the yield of the desired carbamate.

That such decomposition of methyl carbamoyl chloride by aqueous alkali is to be expected is demonstrated by the two experiments described below. In these experiments, methyl carbamoyl chloride in the water-immiscible solvent, methylene chloride, is contacted with aqueous base for a few minutes before S-methyl N-hydroxy-thioacetimidate is added. In Experiment (A), the pH of the aqueous phase is 10.1, and no reaction product is formed, showing that the methyl carbamoyl chloride was destroyed. In Experiment (B), the pH of the aqueous phase was 8.15 to 7.3, and a 52.6% yield of reaction product is obtained, showing that in the presence of a minor amount of base, about half of the methyl carbamoyl chloride is destroyed. Surprisingly, as demonstrated by the Examples of this patent application, we have discovered that the reaction can be carried out in the presence of base at pH 10 and above, without serious decomposition of methyl carbamoyl chloride, if S-methyl N-hydroxythioacetimidate is present while the base and methyl carbamoyl chloride are mixed.

(A) To 233.7 parts of a 22.0% solution of methyl carbamoyl chloride (0.55 mole) in methylene chloride was added within 5 minutes at 20°-25° C with cooling, 112 parts of 19.6% aqueous sodium hydroxide solution (0.55 mole). The pH was then adjusted to 10.1 with 50% sodium hydroxide solution and 52.5 parts of methylthiolacethydroxamate added. Stirring was continued at 20°-25° C for 15 minutes after which time the pH was still at 10.1. The pH of the reaction mass was then adjusted to 7.0 with conc. HCl, the lower, organic layer separated, dried and the solvent removed by evaporation under vacuum to give 54.3 parts of solids, m.p. 83°-87° C, which were identified by infrared analysis as slightly impure methylthioacethydroxamate.

(B) To 233.7 parts of a 22.0% solution of methyl carbamoyl chloride (0.55 mole) in methylene chloride was added within 5 minutes at 20°-25° with cooling, 112 parts of 19.6% aqueous sodium hydroxide solution (0.55 mole). After stirring an additional 5 minutes the pH stabilized at 8.15. Then 52.5 parts of methylthiolacethydroxamate was added and stirring continued for 15 minutes at 20°-25° C, after which time the pH decreased to 7.3. The lower, organic layer was then separated, dried, and the solvent removed by evaporation under vacuum to give 73.6 parts of waxy solids which assayed 57.9% methyl O-(methylcarbamoyl)thiolacethydroxamate by liquid chromatography. This represents a 52.6% yield from methylthiolacethydroxamate.

SUMMARY

According to this invention there is provided an improved process for the preparation of compounds of the following formula:

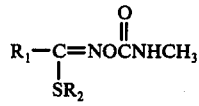

where
$R_1$ is methyl, methoxymethyl, ethyl, or dimethylcarbamoyl;
$R_2$ is alkyl of 1 through 3 carbon atoms or cyanoethyl.

An appropriate N-hydroxythioimidate is reacted with methyl carbamoyl chloride in a mixed solvent system containing water and a water-immiscible organic solvent, at a pH above 10 and a temperature of 0°-80° C:

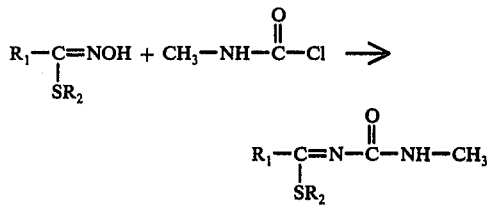

DETAILED DESCRIPTION

Methylcarbamoyl chloride is added, neat or in a solution of an organic solvent, to a solution or suspension of the N-hydroxythiomidate in a mixed solvent system of water and a water immiscible organic solvent, at a pH above 10 and a temperature of 0°-80° C. A preferred pH range is 11-12.5.

The N-hydroxythioimidates suitable for use in this reaction are prepared in the manner disclosed in U.S. Pat. No. 3,787,470 and U.S. Pat. No. 3,658,869.

Methyl carbamoyl chloride is prepared in the manner taught by Slocombe, Hardy, Saunders and Jenkins in JACS 72, 1888-1891 (1950); it can contain up to 40% of the corresponding isocyanate without departing from the concept of this invention.

The reaction of methyl carbamoyl chloride with the N-hydroxythioimidate generates HCl. If this acid is not neutralized or only partially neutralized, undesired side reactions occur resulting in yield loss and impure end product. A distinct feature of this invention is maintenance of the pH of the reaction medium above 10. This can be accomplished by either first adding all of the required amount of base to the solution or suspension of the N-hydroxythioimidate in the water-organic solvent system followed by addition of the carbamoyl chloride, or by simultaneously adding base and carbamoyl chloride. It is preferred to maintain the desired pH by simultaneously adding base and carbamoyl chloride: the pH is permitted to drop to 8-9 only at the very end of the addition of carbamoyl chloride.

The base used is normally aqueous sodium hydroxide or potassium hydroxide. However, alkaline earth hydroxides or organic amines such as triethylamine or pyridine can also be used to maintain a basic pH during the reaction.

The time of reaction, or the time for addition of carbamoyl chloride solution and the solution of base, should be held to a minimum, since contact of the final product with a strong base for an extended period of time will ultimately cause saponification. The reaction time is also determined by the ability to remove the heat of reaction. Generally, reaction times of 15 minutes to several hours are possible, however, it is preferred to complete the reaction within 30-60 minutes.

The temperature of the reaction is generally maintained in the range of 0°-80° C, preferably in the range of 20°-50° C. Since the rate of hydrolysis of the carbamoyl chloride increases with increasing temperatures, it is generally advantageous to maintain a reaction temperature as low as practically possible, either removing the heat of reaction by external cooling or boiling the solvent system at atmospheric pressure or under vacuum.

The molar ratio of carbamoyl chloride (or the mixture of carbarmoyl chloride and isocyanate) to N-hydroxythioimidate used in the reaction is usually in the range of 1.0-1.2, the exact point being dependent on the reaction temperature employed. It should be recognized that excess reagent is necessary only ecause some is lost due to hydrolysis in the basic reaction medium, which eventually leads to the presence of 1,3-dimethyl urea in the reaction product. Consequently, if no excess or less than the molar amounts of carbamoyl chloride is used, decreased amounts of 1,3-dimethyl urea but increased amounts of unreacted N-hydroxythioimidate are found in the reaction product. It is generally preferred to have a minimum of 1,3-dimethyl urea and a minimum of unreacted starting material present in the reaction product. This is achieved, when operating at 40° C, by charging a molar ratio of carbamoyl chloride (or the mixture of carbamoyl chloride and isocyanate)

to N-hydroxythioimidate of 1.075-1.10. At higher reaction temperatures this ratio increases to 1.10-1.20, and at reaction temperatures below 30° C decreases to 1.02-1.05.

The mixed solvent system used in the reaction consists of water and a suitable water-immiscible organic solvent. The function of the organic solvent is two-fold (1) to dissolve the carbamate ester once it is formed, thus minimizing its contact with the very basic aqueous phase and therefore reducing hydrolysis, and (2) to reduce the contact of carbamoyl chloride with water and base, which causes its hydrolysis. Suitable solvents are those which provide good solubility for the carbamoyl chloride and the carbamate ester, such as $CH_2Cl_2$, $CHCl_3$, $CH_3-CHCl_2$, $CH_2=CCl_2$, $CH_2Cl-CH_2Cl$, and aromatic compounds such as benzene, toluene, and xylene.

The volume ratio of water to organic solvent can vary widely. At one extreme, one can start with water only and add all of the organic solvent, in the form of a very dilute solution of the carbamoyl chloride in the organic solvent, together with very concentrated caustic solution. At the other extreme, one can start with organic solvent only and add neat carbamoyl chloride together with very dilute aqueous caustic. In practice, however, it is preferred to start with a volume ratio of water to organic solvent of 0.5-1.5, using 25 ∝ 50% NaOH to maintain the pH and adding approximately a 50% solution of carbamoyl chloride in organic solvent. At the end of the reaction the volume ratio of water to halogenated organic solvent should be in the range of 1.0-1.25, and for the aromatic solvents in the range of 0.1-0.5. For economic reasons, the amount of water and organic solvent should be limited to that necessary to dissolve all components: the sodium chloride in the aqueous phase and carbamate ester in the organic phase.

Economic reasons — high productivity for a given reactor volume — determine the initial concentration of the starting N-hydroxythioimidate in the mixed solvent system. Even though the process works satisfactorily when the starting material is all dissolved in the mixed solvent system at a concentration of about 10%, it is more practical and preferred to start with a slurry of N-hydroxythioimidate in the mixed solvent system and to introduce the necessary additional water and organic solvent with the aqueous caustic and the carbamoyl chloride solution respectively to provide for conditions at the end of the reaction as stated earlier.

Isolation of the product is accomplished by phase separation at the end of the reaction and evaporation of the organic solvent.

EXAMPLE 1

A suspension of 52.5 parts of S-methyl N-hydroxythioacetimidate in 68 parts of water and 67.5 parts chloroform at room temperature is agitated well and the pH adjusted to 12 with 50% sodium hydroxide. Vacuum of 250-300 mm Hg is then established and gradually 107.1 parts of a 48% methylcarbamoyl chloride solution in chloroform is added, maintaining the pH at 11-12.5 by the simultaneous addition of 50% sodium hydroxide. As the reaction proceeds the temperature of the reaction mass rises to 39°-40° C where it is stabilized due to refluxing solvent. The rate of addition of carbamoyl chloride and caustic is regulated in such a way that a gentle reflux is maintained. When all of the carbamoyl chloride solution has been added, the pH is allowed to drop to 8-9, the reaction mass is cooled to room temperature, the organic phase separated, dried and the solvent removed under vacuum to give 78.6 parts of S-methyl N-[(methylcarbamoyl)oxy] thioacetimidate with a purity of 96.0% as determined by liquid chromatographic anaylsis (93.0% yield of pure material).

EXAMPLE 2

A suspension of 52.5 parts of S-methyl N-hydroxythioacetimidate in 24 parts of water and 60 parts methylene chloride at room temperature is well agitated and the pH adjusted to 12 with 25% NaOH. A solution of 102.9 parts of 50% methylcarbamoyl chloride in methylene chloride is then added gradually, maintaining the pH at 11-12.5 by the simultaneous addition of 25% aqueous caustic. As the reaction progresses the temperature rises gradually to 47°-48° C where it stabilizes due to refluxing solvent. The rate of addition of carbamoyl chloride and caustic is regulated in such a way that gentle reflux is maintained. After the addition of all of the carbamoyl chloride, the pH is allowed to drop to 8-9, the reaction mass is then cooled to room temperature, the organic phase separated, dried and the solvent removed under vacuum to give 79.5 parts of S-methyl N-[(methylcarbamoyl)oxy] thioacetimidate with a purity of 96.6% as determined by liquid chromatographic analysis (95% yield of pure material).

The compounds of Table I are prepared by the procedure of Example 2, using the equivalent amounts of the N-hydroxythioimidates listed in place of the S-methyl N-hydroxythioacetimidate.

Table I

| N-hydroxythioimidates | Product |
| --- | --- |
| S-ethyl N-hydroxythio-acetimidate | S-ethyl N-[(methylcarbamoyl)-Oxy] thioacetimidate |
| S-propyl N-hydroxythio acetimidate | S-propyl N-[(methylcarbamoyl)-oxy] thioacetimidate |
| S-(2-cyanoethyl) N-hydroxy-thioacetimidate | S-(2-cyanoethyl) N-[methyl carbamoyl)oxy] thioacetimidate |
| S-methyl N-hydroxy-thiopropionimidate | S-methyl N-[(methylcarbamoyl)-oxy] thiopropionimidate |
| S-methyl N-hydroxy-methoxythioacetimidate | S-methyl N-[(methylcarbamoyl)-oxy] methoxythioacetimidate |

EXAMPLE 3

A well agitated slurry of 52.5 parts S-methyl N-hydroxythioacetimidate in 68 parts water is adjusted to pH 12 with 50% sodium hydroxide and cooled to 20° C. A solution of 152.0 parts of 32.3% methylcarbamoyl chloride in ethylene chloride is then added gradually over a period of about 30-40 minutes maintaining the temperature at 20°-25° C by external cooling and the pH at 11-12.5 by the simultaneous addition of 50% sodium hydroxide. After all the carbamoyl chloride has been added, the pH is allowed to drop to 8 while agitation is continued for another ten minutes. The organic layer is then separated, dried and the solvent removed under vacuum to give S-methyl N-[(methylcarbamoyl)oxy] thioacetimidate in high yield and high purity.

EXAMPLE 4

The pH of a solution of 52.5 parts of S-methyl N-hydroxythioacetimidate in 24 parts water and 67.5 parts chloroform at 40° C in adjusted to 11.5. A solution of 41.1 parts of methylcarbamoyl chloride and 6.3 parts of methylisocyanate in 66 parts of chloroform is gradually added at 40° C over a period of 30-40 minutes maintaining the pH at 11-12 by the simultaneous addition of 83.0 parts of 26.5% sodium hydroxide. When the chloroform solution has been added, the pH is allowed to drop to 8, the reaction mass is cooled to room temperature, the organic phase is separated, dried and the solvent removed under vacuum to give 79.5 parts of S-methyl N-[(methylcarbamoyl)oxy] thioacetimidate with a purity of more than 95%.

EXAMPLE 5

The pH of a suspension of 81.1 parts of S-methyl 1-(dimethylcarbamoyl)-N-hydroxythioformimidate in 100 parts of water and 167 parts methylene chloride at 25° C is adjusted to 11.5. A solution of 102.9 parts of 50% methyl carbamoyl chloride in methylene chloride is then added gradually over a period of 30 minutes maintaining the pH at 11-12 by the simultaneous addition of 25% sodium hydroxide. As the reaction progresses the temperature increases to 40° C where it is maintained by external cooling. After all of the carbamoyl chloride has been added, the pH is allowed to drop to 8, and the reaction mass cooled to room temperature. The organic layer is then separated, dried and the solvent removed under vacuum to give 106.9 parts (97.5% yield) of essentially pure S-methyl 1-(dimethylcarbamoyl)-N-[(methylcarbomyl)oxy] thioformimidate.

EXAMPLE 6

The pH of a suspension of 52.5 parts of S-methyl N-hydroxythioacetimidate in 55 parts water and 86.7 parts toluene at 25° C is adjusted to 12. A solution of 400 parts of 12.3% methylcarbamoylchloride in toluene is then added gradually over a period of 40 minutes maintaining the pH at 11.5-12.5 by the simultaneous addition of 25% sodium hydroxide. As the reaction progresses the temperature increases to 40° C where it is maintained by external cooling. At the end of the reaction, when the pH has reached 8.7, the toluene layer is separated, dried and the solvent removed by evaporation under vacuum to give 73.3 parts of S-methyl N-[(methylcarbamoyl)oxy] thioacetimidate, with a purity of more than 95% (yield >86.0%).

We claim:
1. In the process for preparing compounds of the formula

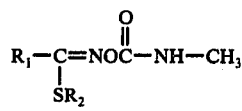

where
R$_1$ is methyl, methoxymethyl, ethyl, or dimethylcarbamoyl; and
R$_2$ is alkyl of 1 through 3 carbon atoms or cyanoethyl; from their corresponding N-hydroxythioimidates and methyl carbamoyl chloride, the improvement which comprises contacting an N-hydroxythioimidate of the formula

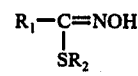

where
R$_1$ and R$_2$ are as defined above, with methyl carbamoyl chloride in a mixed solvent system containing water and a suitable water-immiscible organic solvent with a volume ratio of water to organic solvent of not less than 0.1 at a pH above 10.

2. The process of claim 1 in which the N-hydroxythioimidate reactant has the following substituents:
R$_1$: methyl or dimethylcarbamoyl;
R$_2$: methyl.

3. The process of claim 2 in which the organic solvent is selected from the group consisting of methylene chloride, chloroform and 1,2-dichloroethane.

4. The process of claim 2 in which the N-hydroxythioimidate reactant is S-methyl-N-hydroxythioacetimidate.

5. The process of claim 2 in which the pH is between 11 and 12.5.

* * * * *